(12) United States Patent
Horiuchi

(10) Patent No.: US 6,744,844 B2
(45) Date of Patent: Jun. 1, 2004

(54) IMAGE PRODUCING METHOD AND X-RAY CT APPARATUS

(75) Inventor: Tetsuya Horiuchi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 36 days.

(21) Appl. No.: 10/222,041

(22) Filed: Aug. 16, 2002

(65) Prior Publication Data

US 2003/0035513 A1 Feb. 20, 2003

(30) Foreign Application Priority Data

Aug. 20, 2001 (JP) ........................................ 2001-248630

(51) Int. Cl.$^7$ ................................................. A61B 6/03
(52) U.S. Cl. ............................. 378/15; 378/17; 378/901
(58) Field of Search ............................. 378/4, 8, 15, 17, 378/19, 901

(56) References Cited

U.S. PATENT DOCUMENTS

| | | |
|---|---|---|
| 5,521,955 A | 5/1996 | Gohno et al. |
| 5,590,165 A | 12/1996 | Gohno et al. |
| 5,802,134 A | 9/1998 | Larson et al. |
| 5,881,122 A | 3/1999 | Crawford et al. |
| 5,909,477 A | 6/1999 | Crawford et al. |
| 5,991,356 A | 11/1999 | Horiuchi et al. |
| 6,067,341 A | 5/2000 | Horiuchi |
| 6,118,841 A | 9/2000 | Lai |
| 6,137,858 A | 10/2000 | Horiuchi |
| 6,229,869 B1 | 5/2001 | Hu |
| 6,373,919 B1 | 4/2002 | Horiuchi |
| 6,404,844 B1 | 6/2002 | Horiuchi et al. |
| 6,415,012 B1 | 7/2002 | Taguchi et al. |

*Primary Examiner*—David V Bruce
(74) *Attorney, Agent, or Firm*—Carl B. Horton, Esq.; Armstrong Teasdale LLP

(57) ABSTRACT

In order to obtain an image with artifacts suppressed when a helical scan is conducted employing a multi-row detector with a scan plane tilted, preprocessing such as sensitivity correction is applied to data collected by a helical scan employing a multi-row detector with a scan plane tilted (S1), tilt correcting processing is applied for correcting view-to-view variation of the positions of channels in the detector rows relative to an axis of translation due to the tilt of the scan plane (S2), multi-slice/helical interpolation processing is applied for calculating interpolated data from proximate data in an image reconstruction plane (S3), and backprojection processing is applied to the interpolated data to produce an image (S4).

16 Claims, 10 Drawing Sheets

2_pvn_src[i]

2_pvn_src[i]

IMAGE PRODUCING METHOD AND X-RAY CT APPARATUS

CROSS REFERENCE TO RELATED APPLICATIONS

This application claims the benefit of Japanese Application No. 2001-248630 filed Aug. 20, 2001.

BACKGROUND OF THE INVENTION

The present invention relates to an image producing method and X-ray CT (Computed Tomography) apparatus, and more particularly, to an image producing method and X-ray CT apparatus by which, when a helical scan is conducted employing a multi-row detector having more than one detector row with a scan plane tilted, an image can be obtained with artifacts suppressed.

FIG. 16 is a flow chart showing a prior art image producing method for producing an image based on data obtained by a helical scan employing a multi-row detector having more than one detector row.

In Step S1, preprocessing such as sensitivity correction is applied to the data.

In Step S3, multi-slice/helical interpolation processing is applied for calculating interpolated data from proximate data in an image reconstruction plane.

In Step S4, backprojection processing is applied to the interpolated data to produce an image.

FIG. 17 is a schematic diagram showing exemplary multi-slice/helical interpolation processing using a twin detector.

FIG. 17 expresses the twin detector as viewed from an X-ray tube at a view angle $\pi/2$.

The interpolated data $D(\pi/2, i)$ at the view angle $\pi/2$ for a channel i is calculated by linear interpolation from data $d1(\pi/2, i)$ at the view angle $\pi/2$ for the channel i in a first detector row (j=1) and data $d2(\pi/2, i)$ at the view angle $\pi/2$ for the channel i in a second detector row (j=2).

The linear interpolation is used because the data $d1(\pi/2, i)$ and data $d2(\pi/2, i)$ lie on a line along the subject's body axis, assuming that the CT value varies linearly in the direction of the subject's body axis.

Since the scan plane is not tilted in FIG. 17, the position h1 of the data $d1(\pi/2, i)$ of the first detector row (j=1) relative to the axis of translation is equal to the position h2 of the data $d2(\pi/2, i)$ of the second detector row (j=2) relative to the axis of translation. That is, both the data $d1(\pi/2, i)$ and $d2(\pi/2, i)$ lie on a line along the subject's body axis, which satisfies the condition required for linear interpolation.

When the scan plane is tilted, however, the position h1 of the data $d1(\pi/2, i)$ relative to the axis of translation and the position h2 of the data $d2(\pi/2, i)$ relative to the axis of translation become unequal, as shown in FIG. 18. That is, the data $d1(\pi/2, i)$ and the data $d2(\pi/2, i)$ no longer lie on a line along the subject's body axis. As a result, the condition required for linear interpolation is not satisfied, leading to artifacts.

SUMMARY OF THE INVENTION

It is therefore an object of the present invention is to provide an image producing method and X-ray CT apparatus by which, when a helical scan is conducted employing a multi-row detector having more than one detector row with a scan plane tilted, an image can be obtained with artifacts suppressed.

In accordance with a first aspect, the present invention provides an image producing method for producing an image based on data collected by a helical scan employing a multi-row detector having more than one detector row with a scan plane tilted, characterized in comprising the step of: applying to the data tilt correcting processing for correcting view-to-view variation of the positions of channels in the detector rows relative to an axis of translation due to the tilt of the scan plane.

In the image producing method of the first aspect, tilt correcting processing is newly introduced for correcting view-to-view variation of the positions of channels in the detector rows relative to the axis of translation due to the tilt of the scan plane. Thus, when a helical scan is conducted employing a multi-row detector having more than one detector row with a scan plane tilted, an image can be obtained with artifacts suppressed.

In accordance with a second aspect, the present invention provides an image producing method characterized in comprising the steps of: applying preprocessing such as sensitivity correction to data collected by a helical scan employing a multi-row detector having more than one detector row with a scan plane tilted; next applying tilt correcting processing for correcting view-to-view variation of the positions of channels in the detector rows relative to an axis of translation due to the tilt of the scan plane; applying multi-slice/helical interpolation processing for calculating interpolated data from proximate data in an image reconstruction plane; and applying backprojection processing to the interpolated data to produce an image.

In the image producing method of the second aspect, the tilt correcting processing is applied before the multi-slice/helical interpolation processing for correcting view-to-view variation of the positions of channels in the detector rows relative to the axis of translation due to the tilt of the scan plane. Thus, when a helical scan is conducted employing a multi-row detector having more than one detector row with a scan plane tilted, an image can be obtained with artifacts suppressed using the same multi-slice/helical interpolation processing as conventionally used.

In accordance with a third aspect, the present invention provides the image producing method having the aforementioned configuration, characterized in that said tilt correcting processing includes data position shifting processing for shifting the positions of data arranged in a two-dimensional array along a channel index axis and a view index axis so that the view-to-view variation of the positions of channels in the detector rows relative to the axis of translation due to the tilt of the scan plane is canceled out; data extracting processing for extracting a range of data in which data are completely present for all the views in the view direction from the shifted data array; dummy data appending processing for appending the extracted data with dummy data to adjust the data range; and data transforming processing for transforming the data into data enabling alignment of the channel positions through all views.

In the image producing method of the third aspect, the positions of data are first shifted so that the view-to-view variation of the positions of channels in the detector rows relative to the axis of translation due to the tilt of a scan plane is canceled out. However, the amount of data position shift is not limited to an integer multiple of the channel-to-channel distance. Accordingly, in the shifted data array, there occur concave and convex portions at the opposite ends of the channel index axis, and hence, a portion along the view direction in which data are completely present for all the views and a portion along the view direction that partially lacks data. The portion along the view direction in which data are completely present for all the views can be used as is, and a range of the data corresponding to the portion is extracted. On the other hand, using the portion along the view direction that partially lacks data may cause artifacts, and the portion is discarded. Missing data corresponding to the discarded portion are made up for with dummy data to adjust the data range. Since, as pointed out above, the amount of data position shift is not limited to an integer multiple of the channel-to-channel distance, the data positions in the resulting data array do not match the channel positions for all the views. Therefore, the data are transformed into data enabling alignment of the channel positions through all views by, for example, interpolation. Thus, when a helical scan is conducted employing a multi-row detector having more than one detector row with a scan plane tilted, an image can be obtained with artifacts suppressed using the same multi-slice/helical interpolation processing as conventionally used.

In accordance with a fourth aspect, the present invention provides the image producing method having the aforementioned configuration, characterized in that: said data position shifting processing shifts the positions of parallelized data of the channels in a j-th (j is the detector row index and $1 \leq j \leq J$) detector row by:

$$j\_delt\_iso = Lj \cdot \tan \theta \cdot \sin\{2\pi(pvn-1)/VWN\}$$

in the channel direction, where pvn is the view index and $1 \leq pvn \leq VWN$, rotation is made substantially for $2\pi$ for all views, the tilt angle is represented as $\theta$, and a distance from an intersection of the axis of translation and an axis of rotation to a scan plane corresponding to the j-th detector row is represented as Lj.

The amount of data position shift in the data position shifting processing varies with the conditions of a helical scan (e.g., the helical pitch), and the amount of shift shown in the image producing method of the fourth aspect represents an example.

In accordance with a fifth aspect, the present invention provides the image producing method having the aforementioned configuration, characterized in that: said data extracting processing extracts data from a (Roundup{Lj·tan θ/DMM}+1+j_delt_iso )-th channel to a (I–Roundup{Lj·tan θ/DMM}–1+j_delt_iso )-th channel in the j-th detector row for a pvn-th view, where DMM is the channel-to-channel distance, and Roundup{ } is a roundup function.

The range of data extracted in the data extracting processing varies with the conditions of a helical scan (e.g., the helical pitch), and the range shown in the image producing method of the fifth aspect represents an example.

In accordance with a sixth aspect, the present invention provides the image producing method having the aforementioned configuration, characterized in that said tilt correcting processing includes data extracting processing for extracting data from a (Roundup{Lj* tan θ/DMM}+1+j_delt_iso)-th channel to a (I—Roundup {Lj* tan θ/DMM}–1+j_delt_iso)-th channel in a j-th (j is the detector row index and $1 \leq j \leq J$) detector row for a pvn-th view, where pvn is the view index and $1 \leq pvn \leq VWN$, rotation is made substantially for $2\pi$ for all views, the tilt angle is represented as θ, a distance from an intersection of the axis of translation and the axis of rotation to a scan plane corresponding to the j-th detector row is represented as Lj, DMM is the channel-to-channel distance, Roundup{ } is a roundup function, and $$j\_delt\_iso = Lj^* \tan \theta^* \sin\{2\pi(pvn-1)/VWN\};$$

dummy data appending processing for appending the extracted data with dummy data to adjust the data range; and data transforming processing for transforming the data into data enabling alignment of the channel positions through all views.

In the image producing method of the sixth aspect, while the processing proceeds by sequentially executing the data extracting processing, dummy data appending processing and data transforming processing in this order without data position shifting processing, the same result as that by the image producing method of the fifth aspect can be obtained.

In accordance with a seventh aspect, the present invention provides the image producing method having the aforementioned configuration, characterized in that said dummy data are air data.

In the image producing method of the seventh aspect, air data (the CT value of the air) is used as the dummy data. This provides the best image.

In accordance with an eighth aspect, the present invention provides the image producing method as defined by any one of the inventions of the third aspect through the seventh aspect, characterized in that said data transforming processing is interpolation processing.

Although it is possible to copy the most proximate data and transform the data into data enabling alignment of the channel positions through all views, the image producing method of the eighth aspect uses interpolation processing for the transformation of data into data enabling alignment of the channel positions through all views. This provides the best image.

In accordance with a ninth aspect, the present invention provides an X-ray CT apparatus comprising an X-ray tube, a multi-row detector having more than one detector row opposed to said X-ray tube, translation control means for translating said X-ray tube and said multi-row detector along an axis of translation relative to a subject, rotation control means for rotating at least one of said X-ray tube and said multi-row detector around an axis of rotation, tilt control means for tilting the angle of a scan plane formed by said rotation relative to the axis of translation to an angle other than 90°, scan control means for collecting data by a helical scan employing said multi-row detector with the scan plane tilted, and image producing means for producing an image based on the collected data, characterized in that said X-ray CT apparatus further comprises: tilt correcting processing means for applying to the data tilt correcting processing for correcting view-to-view variation of the positions of channels in the detector rows relative to the axis of translation due to the tilt of the scan plane.

The X-ray CT apparatus of the ninth aspect can suitably implement the image producing method of the first aspect.

In accordance with a tenth aspect, the present invention provides an X-ray CT apparatus comprising an X-ray tube, a multi-row detector having more than one detector row opposed to said X-ray tube, translation control means for translating said X-ray tube and said multi-row detector along an axis of translation relative to a subject, rotation control means for rotating at least one of said X-ray tube and said multi-row detector around an axis of rotation, tilt control means for tilting the angle of a scan plane formed by said rotation relative to the axis of translation to an angle other than 90°, scan control means for collecting data by a helical scan employing said multi-row detector with the scan plane tilted, and image producing means for producing an image based on the collected data, characterized in that said X-ray CT apparatus further comprises: preprocessing means for applying preprocessing such as sensitivity correction to said data; tilt correcting processing means for applying tilt correcting processing for correcting view-to-view variation of the positions of channels in the detector rows relative to the axis of translation due to the tilt of the scan plane; multi-slice/helical interpolation processing means for applying multi-slice/helical interpolation processing for calculating interpolated data from proximate data in an image reconstruction plane; and backprojection processing means for applying backprojection processing to the interpolated data to produce an image.

The X-ray CT apparatus of the tenth aspect can suitably implement the image producing method of the second aspect.

In accordance with an eleventh aspect, the present invention provides the X-ray CT apparatus having the aforementioned configuration, characterized in that said tilt correcting processing means comprises: data position shifting means for shifting the positions of data arranged in a two-dimensional array along a channel index axis and a view index axis so that the view-to-view variation of the positions of channels in the detector rows relative to the axis of translation due to the tilt of the scan plane is canceled out; data extracting means for extracting a range of data in which data are completely present for all the views in the view direction from the shifted data array; dummy data appending means for appending the extracted data with dummy data to adjust the data range; and data transformation means for transforming the data into data enabling alignment of the channel positions through all views.

The X-ray CT apparatus of the eleventh aspect can suitably implement the image producing method of the third aspect.

In accordance with a twelfth aspect, the present invention provides the X-ray CT apparatus having the aforementioned configuration, characterized in that: said data position shifting means shifts the positions of parallelized data of the channels in a j-th (is the detector row index and $1 \leq j \leq J$) detector row by:

$$j\_delt\_iso = Lj \cdot \tan\theta \cdot \sin\{2\pi(pvn-1)/VWN\}$$

in the channel direction, where pvn is the view index and $1 \leq pvn \leq VWN$, rotation is made substantially for $2\pi$ for all views, the tilt angle is represented as $\theta$, and a distance from an intersection of the axis of translation and the axis of rotation to a scan plane corresponding to the j-th detector row is represented as Lj.

The X-ray CT apparatus of the twelfth aspect can suitably implement the image producing method of the fourth aspect.

In accordance with a thirteenth aspect, the present invention provides the X-ray CT apparatus having the aforementioned configuration, characterized in that: said data extracting means extracts data from a (Roundup{Lj·tan θ/DMM}+1+j_delt_iso )-th channel to a (I−Roundup{Lj·tan θ/DMM}−1+j_delt_iso)-th channel in the j-th detector row for a pvn-th view, where DMM is the channel-to-channel distance, and Roundup{ } is a roundup function.

The X-ray CT apparatus of the thirteenth aspect can suitably implement the image producing method of the fifth aspect.

In accordance with a fourteenth aspect, the present invention provides the X-ray CT apparatus having the aforementioned configuration, characterized in that said tilt correcting means comprises: data extracting means for extracting data from a (Roundup{Lj·tan θ/DMM}+1+j_delt_iso)-th channel to a (I−Roundup{Lj·tan θ/DMM}−1+j_delt_iso)-th channel in a j-th (j is the detector row index and $1 \leq j \leq J$) detector row for a pvn-th view, where pvn is the view index and $1 \leq pvn \leq VWN$, rotation is made substantially for $2\pi$ for all views, the tilt angle is represented as $\theta$, a distance from an intersection of the axis of translation and the axis of rotation to a scan plane corresponding to the j-th detector row is represented as Lj, DMM is the channel-to-channel distance, Roundup{ } is a roundup function, and $$j\_delt\_iso = Lj \cdot \tan\theta \cdot \sin\{2\pi(pvn-1)/VWN\};$$

dummy data appending means for appending the extracted data with dummy data to adjust the data range; and data transformation means for transforming the data into data enabling alignment of the channel positions through all views.

The X-ray CT apparatus of the fourteenth aspect can suitably implement the image producing method of the sixth aspect.

In accordance with a fifteenth aspect, the present invention provides the X-ray CT apparatus having the aforementioned configuration, characterized in that said dummy data are air data.

The X-ray CT apparatus of the fifteenth aspect can suitably implement the image producing method of the seventh aspect.

In accordance with a sixteenth aspect, the present invention provides the X-ray CT apparatus having the aforementioned configuration, characterized in that said data transforming means is interpolating means.

The X-ray CT apparatus of the sixteenth aspect can suitably implement the image producing method of the eighth aspect.

According to the image producing method and X-ray CT apparatus, when a helical scan is conducted employing a multi-row detector with a scan plane tilted, an image can be obtained with artifacts suppressed. Thus, a tilted scan can be performed circumventing portions that are desirably kept out of radiation exposure (e.g., a fetus) or portions that cause artifacts when irradiated with X-rays (e.g., a portion embedded with a metal).

Further objects and advantages of the present invention will be apparent from the following description of the preferred embodiments of the invention as illustrated in the accompanying drawings.

DETAILED DESCRIPTION OF THE INVENTION

Embodiments of the present invention will now be described with reference to the accompanying drawings.

First Embodiment

Figure 1A:
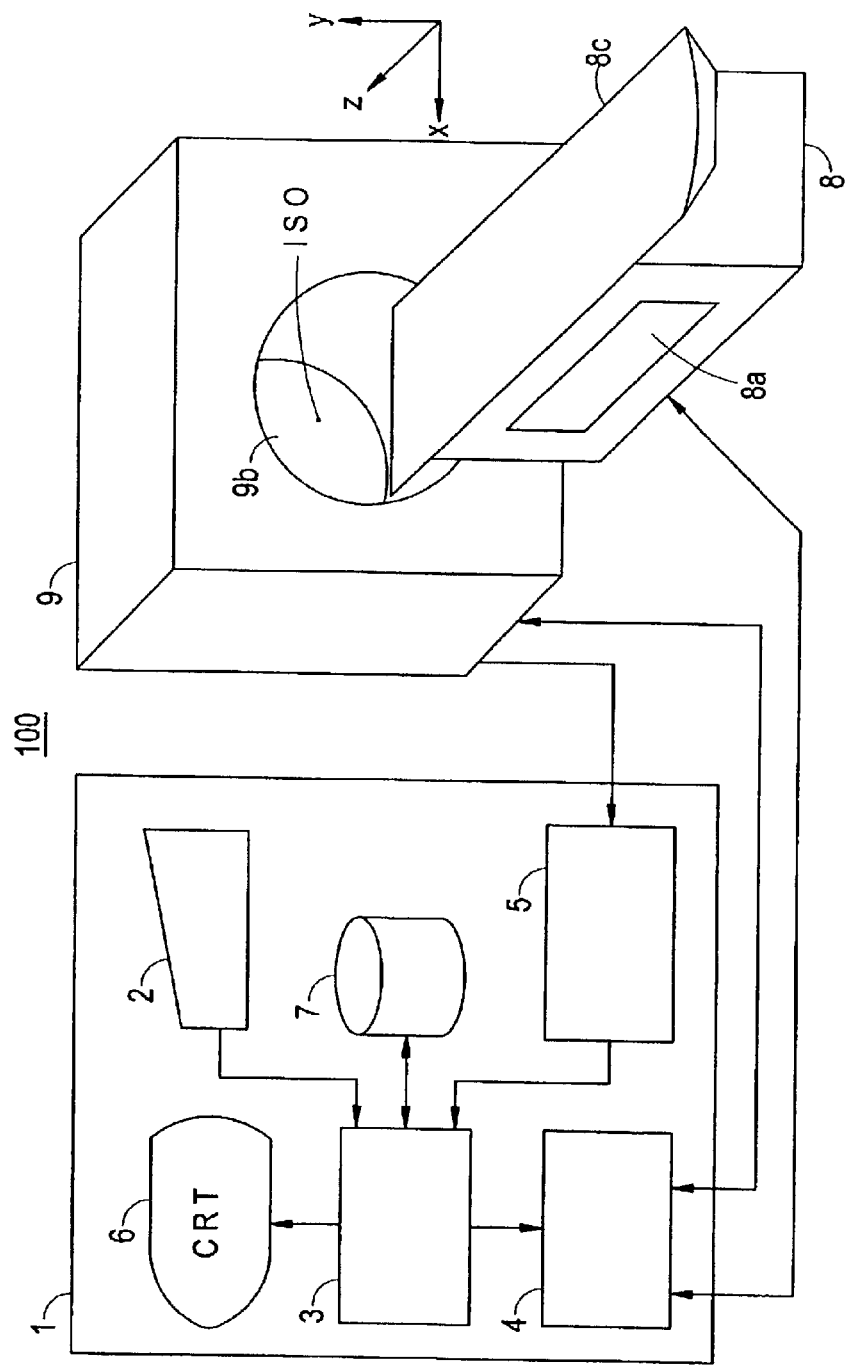
FIG. 1 is a block diagram of an X-ray CT apparatus in accordance with a first embodiment.
Figure 1B:
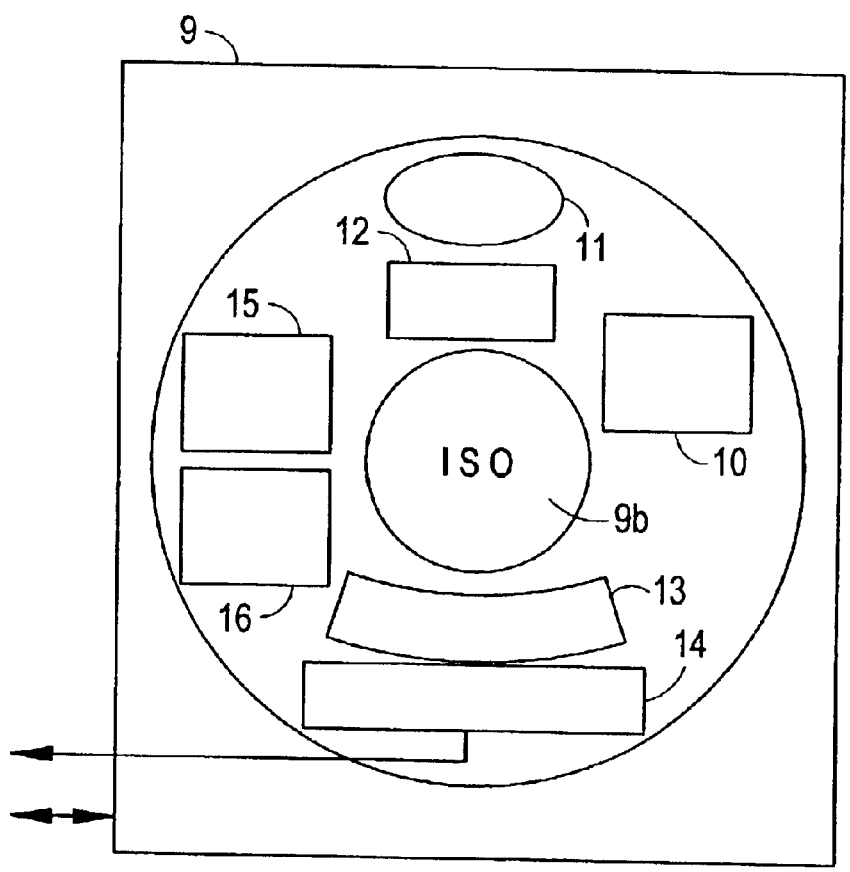

FIG. 1 is a block diagram of an X-ray CT apparatus 100 in accordance with a first embodiment of the present invention.

The X-ray CF apparatus 100 comprises an operation console 1, a table apparatus 8 and a scan gantry 9.

The operation console 1 comprises an input device 2 for receiving commands and information input by an operator, a central processing apparatus 3 for executing scan processing and image producing processing, a control interface 4 for communicating control signals with the imaging table 8 and scan gantry 9, a data collection buffer 5 for collecting data acquired at the scan gantry 9, a CRT 6 for displaying an image reconstructed from the data, and a storage device 7 for storing programs, data and images.

The table apparatus 8 comprises a cradle 8c for resting a subject, and a movement controller 8a for moving the cradle 8c in z- and y-axis directions.

The y-axis represents the vertical direction, and the z-axis represents the longitudinal direction of the cradle 8c. Moreover, the axis orthogonal to the y- and z-axes is represented by an x-axis. The subject's body axis extends along the z-axis direction.

The scan gantry 9 comprises an X-ray controller 10, an X-ray tube 11, a collimator 12, a multi-row detector 13 having more than one detector row, a data collecting section 14, a rotation controller 15 for rotating the X-ray tube 11 and multi-row detector 13 etc. around an isocenter ISO, and a tilt controller 16 for tilting the angle of a scan plane.

Figure 2:
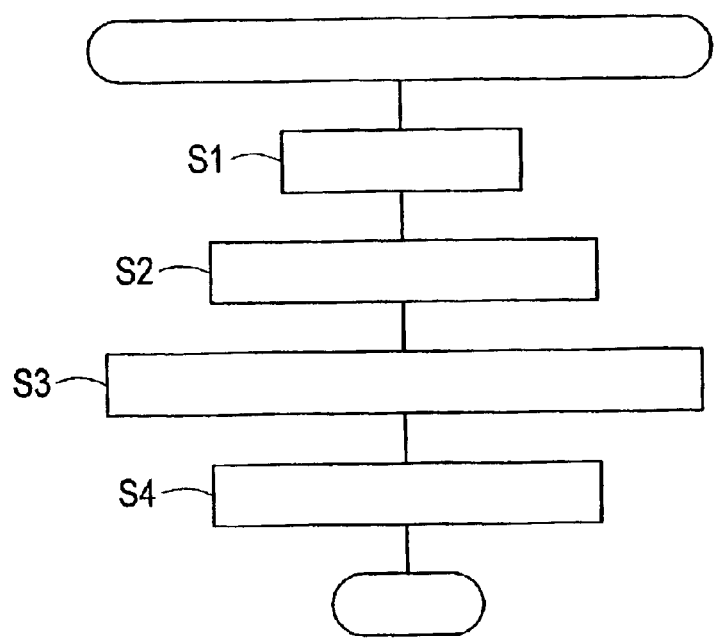
FIG. 2 is a flow chart of image producing processing in accordance with the first embodiment.

FIG. 2 is a flow chart of image producing processing by the X-ray CT apparatus 100.

In Step S1, preprocessing such as sensitivity correction is applied to data collected by a helical scan involving rotating the X-ray tube 11 and multi-row detector 13 etc. around the isocenter ISO while translating the cradle 8c with respect to the scan gantry 9 with a scan plane tilted.

In Step S2, tilt correcting processing is applied for correcting view-to-view variation of the positions of channels in the detector rows relative to the axis of translation due to the tilt of the scan plane. The tilt correcting processing will be described in detail later.

In Step S3, multi-slice/helical interpolation processing is applied for calculating interpolated data from proximate data in an image reconstruction plane.

In Step S4, backprojection processing is applied to the interpolated data to produce an image.

Steps S1, S3 and S4 are the same as those in the conventional processing.

Figure 3:
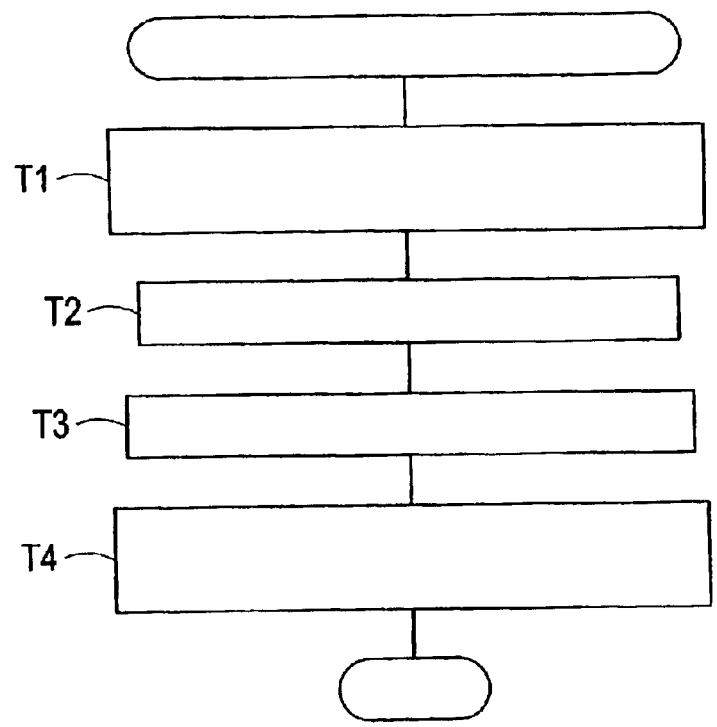
FIG. 3 is a flow chart of tilt correcting processing in accordance with the first embodiment.

FIG. 3 is a flow chart showing the tilt correcting processing.

In Step T1, the data are arranged in a two-dimensional array along a channel index axis and a view index axis, and the positions of the data are then shifted so that the view-to-view variation of the positions of channels in the detector rows relative to the axis of translation due to the tilt of a scan plane is canceled out. An example of the data position shifting processing will be described later.

In Step T2, a range of data in which data are completely present for all the views in the view direction is extracted from the shifted data array. An example of the data extracting processing will be described later.

In Step T3, the extracted data are appended with dummy data to adjust the data range. An example of the dummy data appending processing will be described later.

In Step T4, the data are transformed into data enabling alignment of the channel positions through all views. An example of the data transforming processing will be described later.

The examples will next be described.

In these examples, a helical scan involves a rotation substantially for $2\pi$ for all views (views for one cycle) and a translation by a slice width for the $2\pi$ rotation (i.e., helical pitch=1), where the tilt angle is represented as $\theta$, and a distance from an intersection (isocenter ISO) of the axis of translation and the axis of rotation to a scan plane corresponding to a j-th detector row is represented as Lj.

Moreover, the view angle $\phi=0$ and the view index pvn=1 when the multi-row detector 13 is positioned just below in the vertical direction.

Figure 4:
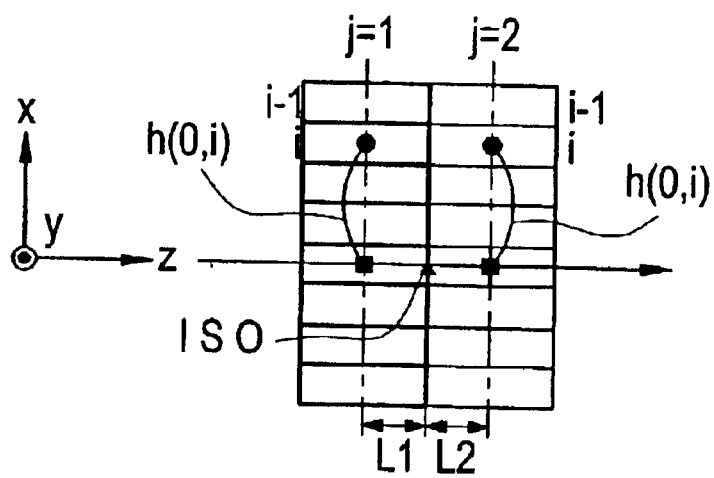
FIG. 4 is an explanatory diagram showing the position of an i-th channel relative to an axis of translation at a view angle φ=0.

FIG. 4 shows a twin detector when the view angle $\phi=0$.

A position h1(0, i) of an i-th channel in a first detector row (j=1) relative to the axis of translation is equal to a position h2(0, i) of the i-th channel in a second detector row (j=2) relative to the axis of translation regardless of the tilt angle $\theta$.

Figure 5:
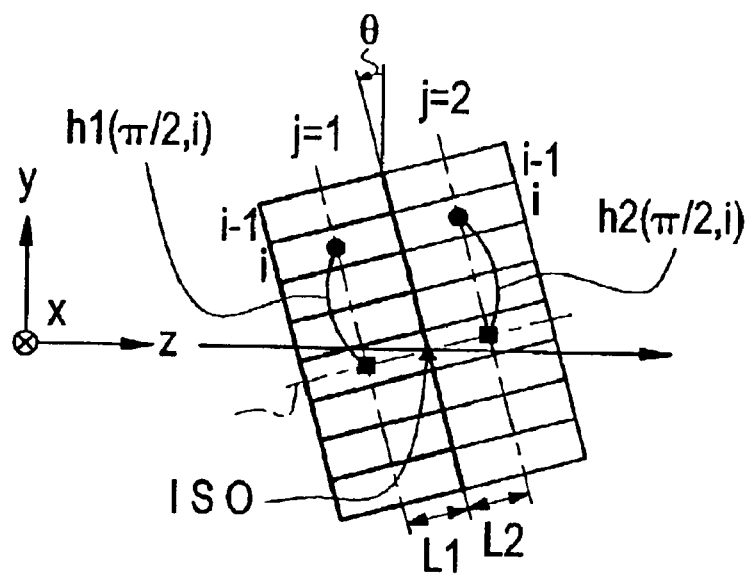
FIG. 5 is an explanatory diagram showing the position of the i-th channel relative to the axis of translation at a view angle φ=π/2.

FIG. 5 shows the twin detector when the view angle $\phi=\pi/2$.

A position h1($\pi/2$, i) of an i-th channel in the first detector row (j=1) relative to the axis of translation is not equal to a position h2($\pi/2$, i) of the i-th channel in the second detector row (j=2) relative to the axis of translation because of the tilt angle $\theta$.

Figure 6:
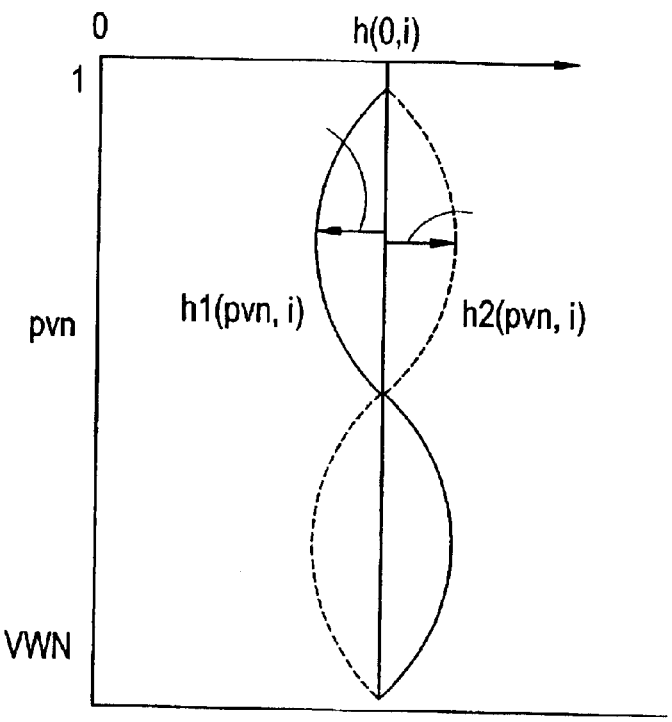
FIG. 6 is an explanatory diagram showing view-to-view variation of the position of the i-th channel relative to the axis of translation due to a tilt of a scan plane.

FIG. 6 shows that a position h1(pvn, i) of an i-th channel in a first detector row (j=1) relative to the axis of translation and a position h2(pvn, i) of the i-th channel in a second detector row (j=2) relative to the axis of translation vary from view to view due to the tilt of a scan plane. When the view index is represented as pvn and $1 \leq pvn \leq VWN$, a position hj(pvn, i) is generally expressed by the following equation:

$$hj(pvn,i)=h(0, i)+j\_delt\_iso\_max \cdot \sin\{2\pi(pvn-1)/VWN\}.$$

The view angle $\phi=2\pi(pvn-1)/VWN$.

Figure 7:
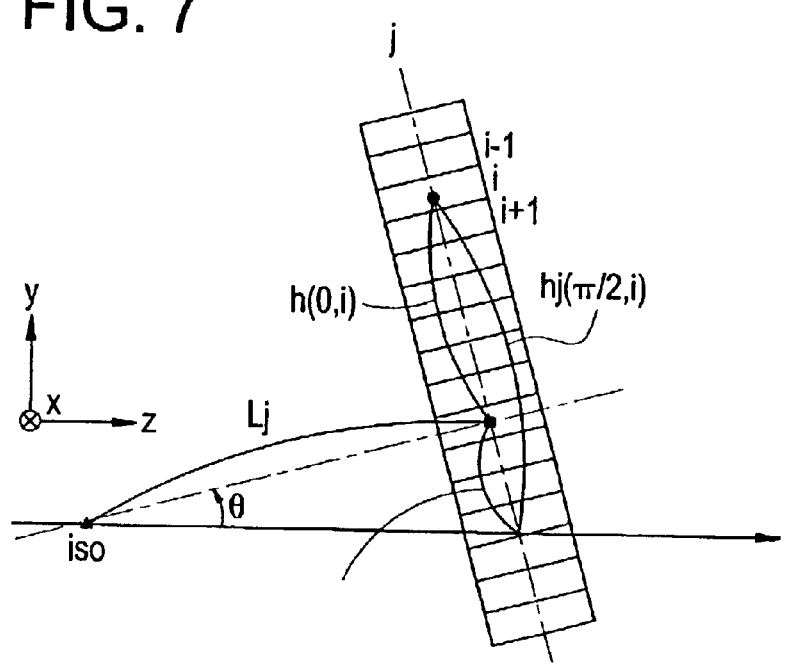
FIG. 7 is an explanatory diagram showing a j-th channel at a view angle φ=π/2.

FIG. 7 shows a j-th detector row when the view angle $\phi=\pi/2$.

As can be seen from FIG. 7, $$j\_delt\_iso\_max=Lj\cdot\tan\theta.$$

Figure 8:
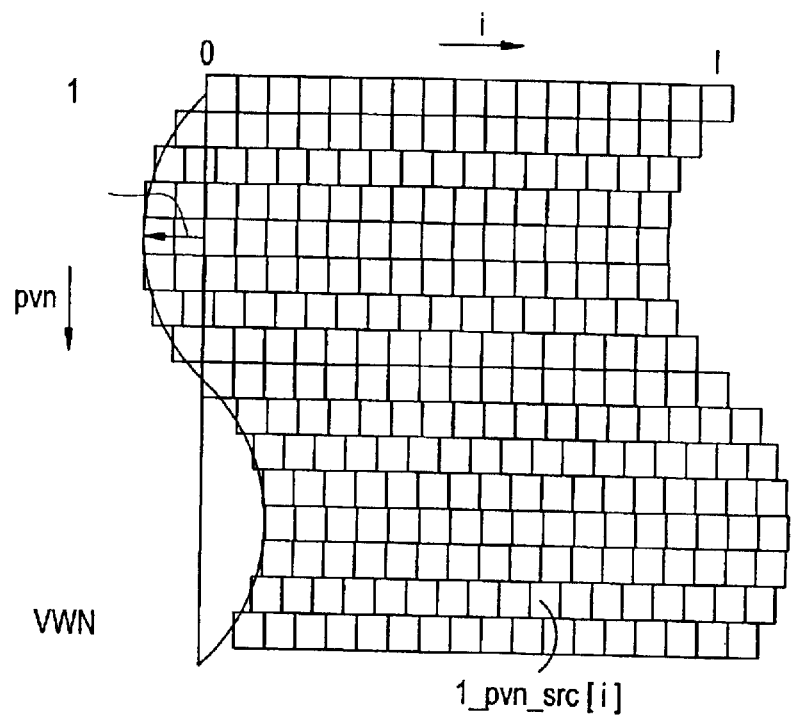
FIG. 8 is a diagram explaining data position shifting processing for a first detector row in a twin detector.

FIG. 8 is a diagram for explaining the data position shifting processing for the first detector row (j=1) in the twin detector.

The data are arranged in a two-dimensional array along a channel index axis and a view index axis, and the data position for a view index pvn is then shifted by:

$$1\_delt\_iso\_max\cdot\sin\{(pvn-1)/VWN\}$$

in the channel index direction. The positions of the data on a line in the view index direction relative to the axis of translation become the same in the shifted data array shown in FIG. 8.

Figure 9:
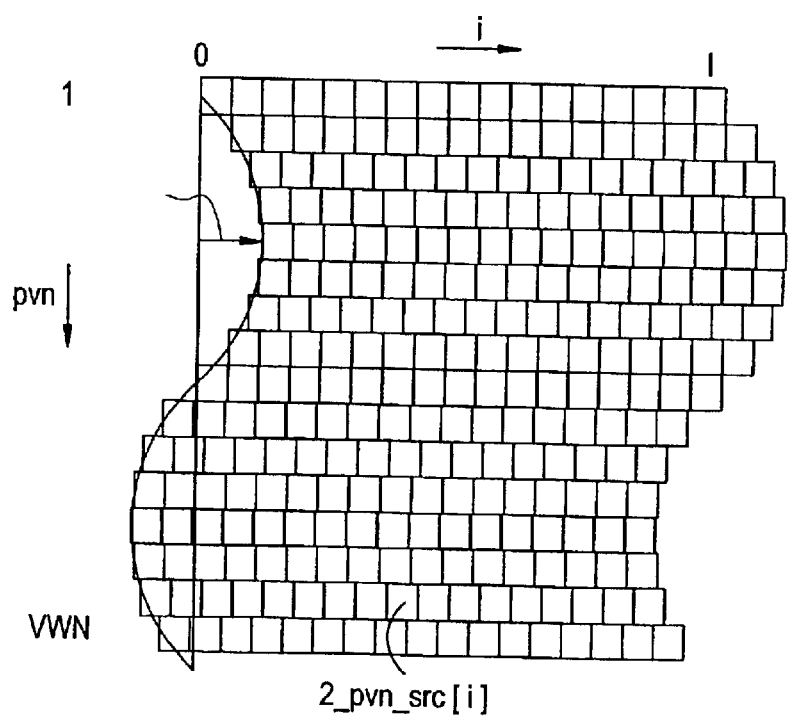
FIG. 9 is a diagram explaining the data position shifting processing for a second detector row in the twin detector.

FIG. 9 is a diagram for explaining the data position shifting processing for the second detector row (j=2) in the twin detector.

The data are arranged in a two-dimensional array along a channel index axis and a view index axis, and the data position for a view index pvn is then shifted by:

$$2\_delt\_iso\_max\cdot\sin\{(pvn-1)/VWN\}$$

in the channel index direction. The positions of the data on a line in the view index direction relative to the axis of translation become the same in the shifted data array shown in FIG. 9.

Figure 10:
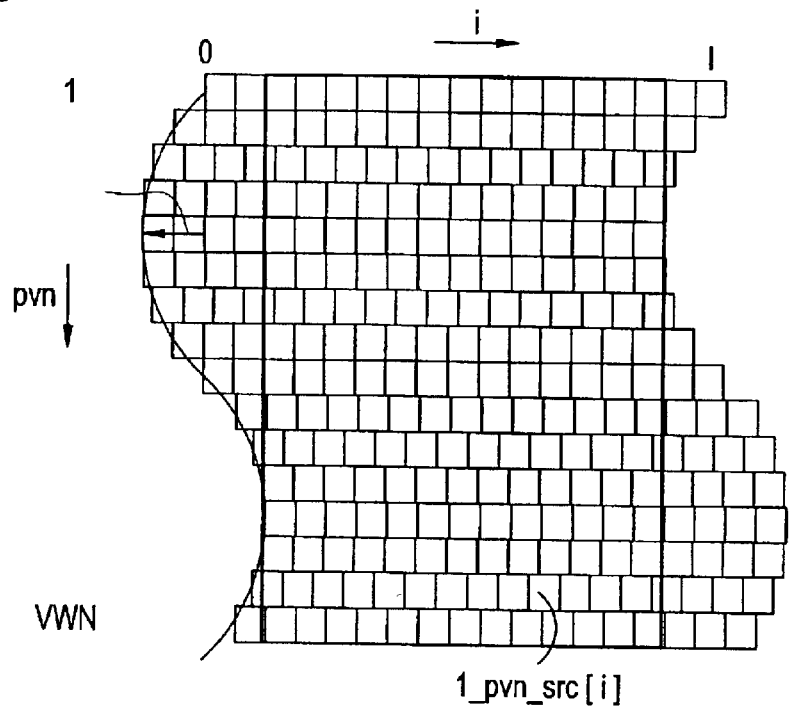
FIG. 10 is a diagram explaining data extracting processing for the first detector row in the twin detector.

FIG. 10 is a diagram for explaining the data extracting processing for the first detector row (j=1) in the twin detector.

From the data array subjected to the data position shifting, a range of data (surrounded by solid line) in which data are completely present for all the views in the view direction is extracted.

The extracted range is generally represented as from a (Roundup{Lj·tan θ/DMM}+1+j_delt_iso)-th channel to a (I−Roundup{Lj·tan θ/DMM}−1+j_delt_iso)-th channel in a j-th detector row for a pvn-th view, where DMM is the channel-to-channel distance, and Roundup{ } is roundup function.

Figure 11:
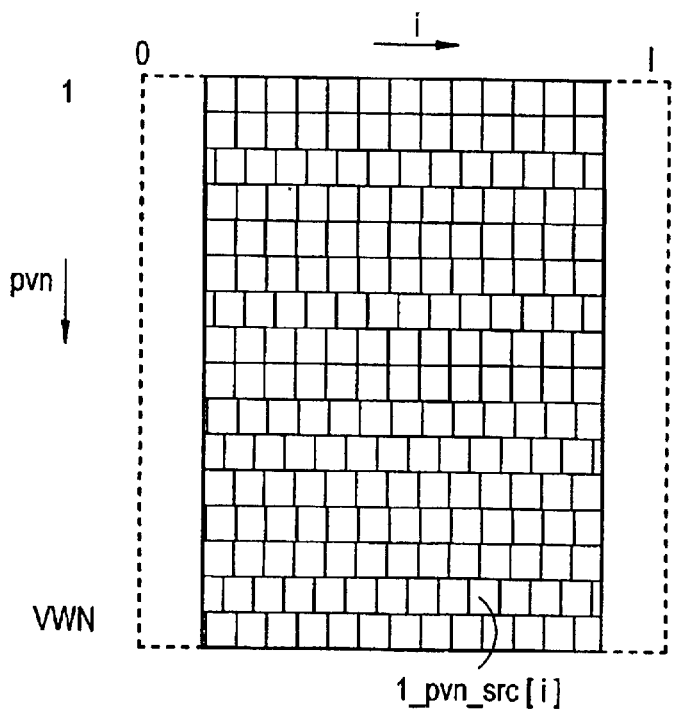
FIG. 11 is a diagram explaining dummy data appending processing for the first detector row in the twin detector.

FIG. 11 is a diagram for explaining the dummy data appending processing for the first detector row (j=1) in the twin detector.

The extracted data array is appended with air data, and the data range of the array is adjusted to the original data array.

Figure 12:
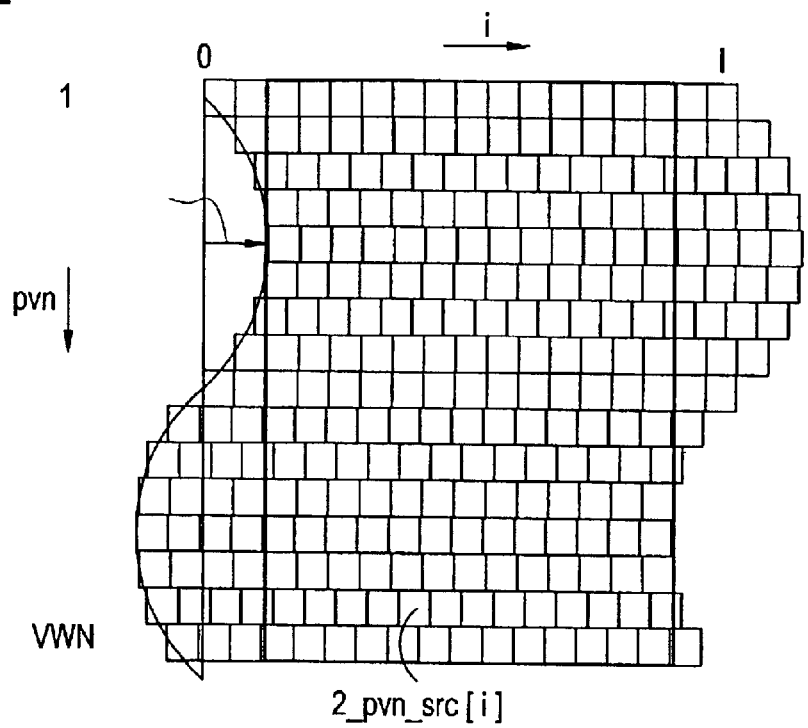
FIG. 12 is a diagram explaining the data extracting processing for the second detector row in the twin detector.

FIG. 12 is a diagram for explaining the data extracting processing for the second detector row (j=2) in the twin detector.

From the data array subjected to the data position shifting, a range of data (surrounded by solid line) in which data are completely present for all the views in the view direction is extracted.

Figure 13:
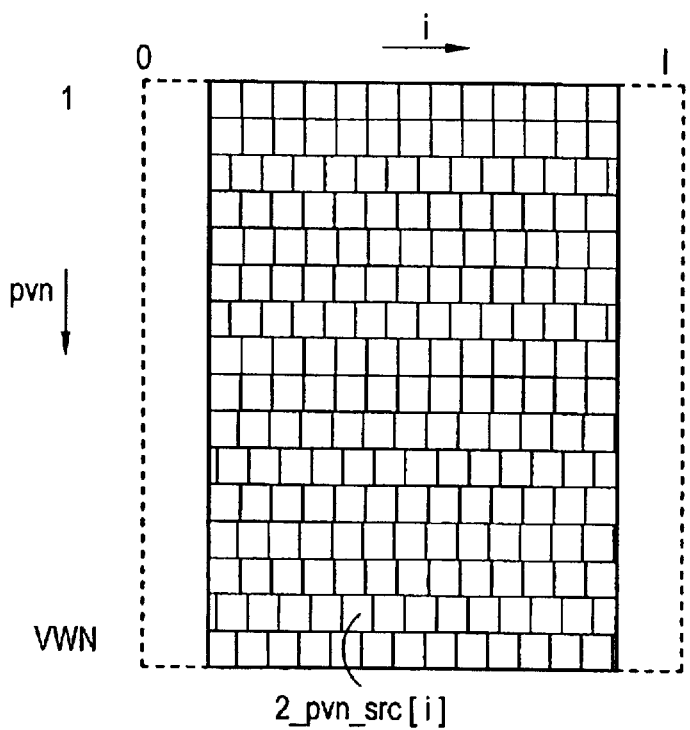
FIG. 13 is a diagram explaining the dummy data appending processing for the second detector row in the twin detector.

FIG. 13 is a diagram for explaining the dummy data appending processing for the second detector row (j=2) in the twin detector.

The extracted data array is appended with air data, and the data range of the array is adjusted to the original data array.

Figure 14:
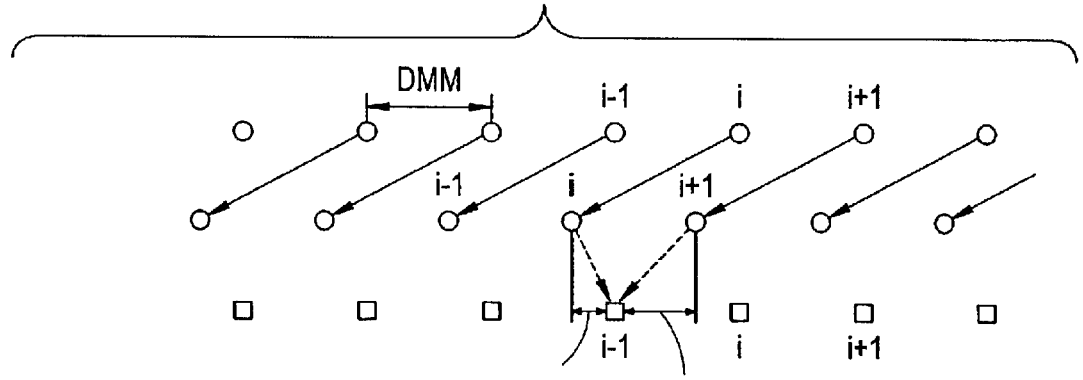
FIG. 14 is a diagram explaining data transforming processing by linear interpolation.

FIG. 14 is a diagram for explaining the data transforming processing by linear interpolation.

src[i] represents data of channels for a certain view in the original data array.

The positions of data are shifted by the data position shifting processing.

Hence, data dest[i] at the original position is calculated by the linear interpolation processing.

When the data are shifted to lower channel indices as shown in FIG. 14, the linear interpolation processing gives:

$$delt\_iso=delt\_iso\_max\cdot\sin\{2\pi(pvn-1)/VWN\}$$

$$int\_delt\_iso=abs\{int\{delt\_iso/DMM\}\}$$

$$ratio=abs\{delt\_iso/DMM\}-int\_delt\_iso$$

$$dest[i-int\_delt\_iso]=src[i]\cdot(1-ratio)+src[i+1]\cdot ratio$$

where int{ } is an integer extracting function and abs{ } is an absolute function. On the other hand, when the data are shifted to higher channel indices, $$dest[i+int\_delt\_iso]=src[i]\cdot(1-ratio)+src[i+1]\cdot ratio.$$

According to the X-ray CF apparatus 100 above, when the multi-row detector 13 is employed and a helical scan is conducted with a scan plane tilted, an image can be obtained with artifacts suppressed.

Second Embodiment

Figure 15:
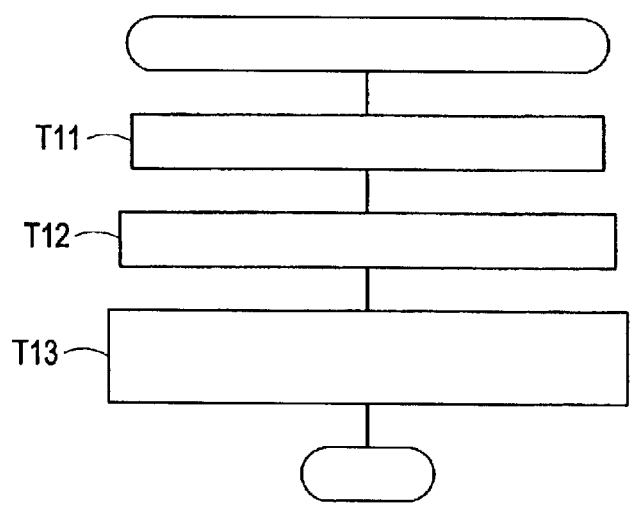
FIG. 15 is a flow chart of the tilt correcting processing in accordance with a second embodiment.
Figure 16:
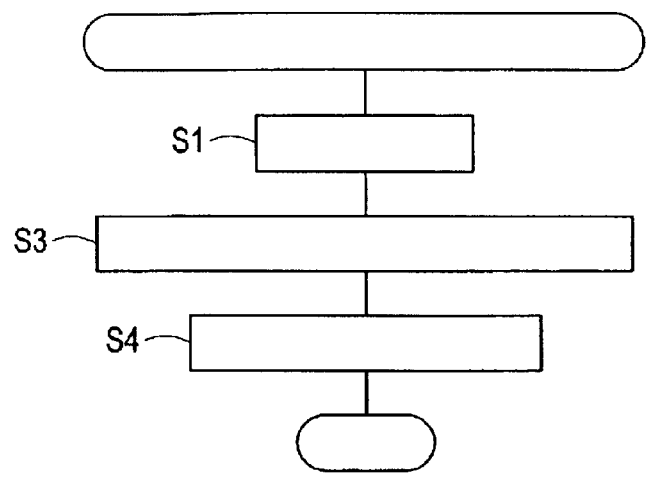
FIG. 16 is a flow chart showing conventional image producing processing.
Figure 17:
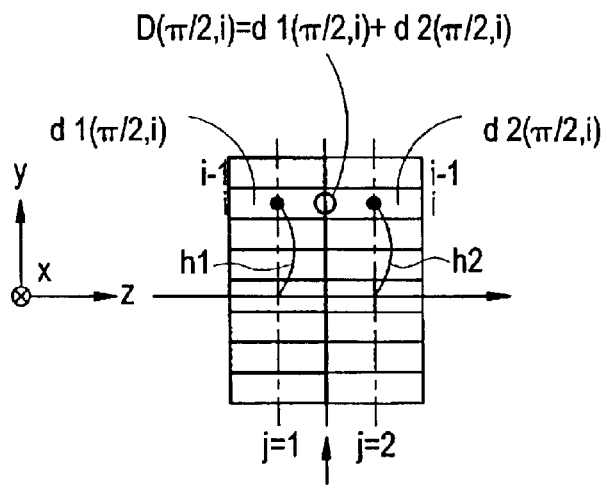
FIG. 17 is an explanatory diagram showing the position of an i-th channel relative to an axis of translation at a view angle $\phi=\pi/2$ without tilting.
Figure 18:
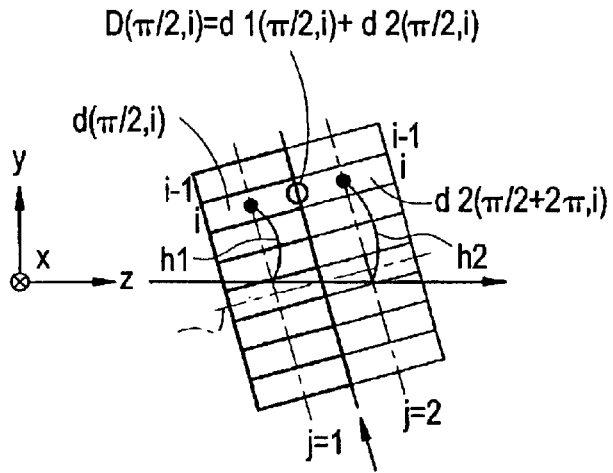
FIG. 18 is an explanatory diagram showing the position of the i-th channel relative to the axis of translation at a view angle $\phi=\pi/2$ with tilting.

FIG. 15 is a flow chart of the tilt correcting processing in a second embodiment.

In Step T11, data from a (Roundup{Lj·tan θ/DMM}+1+j_delt_iso)-st channel to a (I−Roundup{Lj·tan θ/DMM}−1+j_delt_iso)-st channel in a j-th detector row for a pvn-th view are extracted.

In Step T12, the extracted data are appended with dummy data to adjust the data range among the views.

In Step T13, the data positions are shifted to construct a two-dimensional data array like the original data, as shown in FIGS. 11 and 13. Then, the data are transformed into data enabling alignment of the channel positions through all views.

The second embodiment is substantially equivalent to the first embodiment, except that the data position shifting processing follows the dummy data appending processing.

The data position shifting processing may be executed after the data extracting processing, and the dummy data appending processing may be executed thereafter.

Although the data are assumed to be parallelized data collected by the fan-beam type X-ray CT apparatus 100 in the preceding description, the tilt correcting processing may be applied to data before parallelization.

Moreover, although a twin detector is employed in the examples in the preceding description, the present invention can be readily applied to a multi-row detector having three or more detector rows.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray CT apparatus comprising:
   an X-ray tube;
   a multi-row detector having more than one detector row opposed to said X-ray tube;
   a translation control device for translating said X-ray tube and said multi-row detector along an axis of translation relative to a subject;
   a rotation control device for rotating at least one of said X-ray tube and said multi-row detector around an axis of rotation,
   a tilt control device for tilting the angle of a scan plane formed by said rotation relative to the axis of translation to an angle other than 90°, a scan control device for collecting data by a helical scan employing said multi-row detector with the scan plane tilted;

an image producing device for producing an image based on the collected data; and a tilt correcting processing device for applying to the data tilt correcting processing for correcting view-to-view variation of the positions of channels in the detector rows relative to the axis of translation due to the tilt of the scan plane, wherein said tilt correcting processing device comprises:

a data extracting device for extracting data from a (Roundup{Lj* tan θ/DMM}+1+j_delt_iso)-th channel to a (I—Roundup{Lj* tan θ/DMM}−1+j_delt_iso)-th channel in a j-th (j is the detector row index and 1≦j≦J) detector row for a pvn-th view, where pvn is the view index and 1≦pvn≦VWN, rotation is made substantially for 2π for all views, the tilt angle is represented as θ, a distance from an intersection of the axis of translation and the axis of rotation to a scan plane corresponding to the j-th detector row is represented as Lj, DMM is the channel-to-channel distance, Roundup { } is a roundup function, and $$j\_delt\_iso = Lj^* \tan \theta^* \sin\{2\pi(pvn-1)/VWN\}$$

a dummy data appending device for appending the extracted data with dummy data to adjust the data range; and a data transformation device for transforming the data into data enabling alignment of the channel positions through all views.

2. An image producing method for producing an image based on data collected by a helical scan employing a multi-row detector having more than one detector row with a scan plane tilted, comprising the step of:

applying to the data tilt correcting processing for correcting view-to-view variation of the positions of channels in the detector rows relative to an axis of translation due to the tilt of the scan plane, wherein said tilt correcting processing includes;

data position shifting processing for shifting the positions of data arranged in a two-dimensional array along a channel index axis and a view index axis so that the view-to-view variation of the positions of channels in the detector rows relative to the axis of translation due to the tilt of the scan plane is canceled out;

data extracting processing for extracting a range of data in which data are completely present for all the views in the view direction from the shifted data array;

dummy data appending processing for appending the extracted data with dummy data to adjust the data range; and data transforming processing for transforming the data into data enabling alignment of the channel positions through all views.

3. The image producing method of claim 2, wherein said data position shifting processing shifts the positions of parallelized data of the channels in a j-th (j is the detector row index and 1≦j≦J) detector row by $$j\_delt\_iso = Lj^* \tan \theta^* \sin\{2\pi(pvn-1)/VWN\}$$

in the channel direction, where pvn is the view index and 1≦pvn≦VWN, rotation is made substantially for 2π for all views, the tilt angle is represented as θ, and a distance from an intersection of the axis of translation and an axis of rotation to a scan plane corresponding to the j-th detector row is represented as Lj.

4. The image producing method of claim 3, wherein said data extracting processing extracts data from a (Roundup{Lj* tan θ/DMM}+1+j_delt_iso)-th channel to a (I—Roundup {Lj* tan θ/DMM}−1+j_delt_iso)-th channel in the j-th detector row for a pvn-th view, where DMM is the channel-to-channel distance, and Roundup { } is a roundup function.

5. The image producing method of claim 2, wherein said data transforming processing is interpolation processing.

6. The image producing method of claim 2, wherein said dummy data are air data.

7. An image producing method for producing an image based on data collected by a helical scan employing a multi-row detector having more than one detector row with a scan plane tilted, comprising the step of:

applying to the data tilt correcting processing for correcting view-to-view variation of the positions of channels in the detector rows relative to an axis of translation due to the tilt of the scan plane, wherein said tilt correcting processing includes:

data extracting processing for extracting data from a (Roundup{Lj* tan θ/DMM}+1j_delt_iso)-th channel to a (I—Roundup{Lj* tan θ/DMM}−1+j_delt_iso)-th channel in a j-th (j is the detector row index and 1≦j≦J) detector row for a pvn-th view, where pvn is the view index and 1≦pvn≦VWN, rotation is made substantially for 2π for all views, the tilt angle is represented as θ, a distance from an intersection of the axis of translation and the axis of rotation to a scan plane corresponding to the j-th detector row is represented as Lj, DMM is the channel-to-channel distance, Roundup { } is a roundup function, and $$j\_delt\_iso = Lj^* \tan \theta^* \sin\{2\pi(pvn-1)/VWN\}$$

dummy data appending processing for appending the extracted data with dummy data to adjust the data range; and data transforming processing for transforming the data into data enabling alignment of the channel positions through all views.

8. The image producing method of claim 7, wherein said dummy data are air data.

9. The image producing method of claim 7, wherein said data transforming processing is interpolation processing.

10. An X-ray CT apparatus comprising:

an X-ray tube;

a multi-row detector having more than one detector row opposed to said X-ray tube;

a translation control device for translating said X-ray tube and said multi-row detector along an axis of translation relative to a subject;

a rotation control device for rotating at least one of said X-ray tube and said multi-row detector around an axis of rotation, a tilt control device for tilting the angle of a scan plane formed by said rotation relative to the axis of translation to an angle other than 90°, a scan control device for collecting data by a helical scan employing said multi-row detector with the scan plane tilted;

an image producing device for producing an image based on the collected data; and a tilt correcting processing device for applying to the data tilt correcting processing for correcting view-to-view variation of the positions of channels in the detector rows relative to the axis of translation due to the tilt of the scan plane, wherein said tilt correcting processing device comprises:
  a data position shifting device for shifting the positions of data arranged in a two-dimensional array along a channel index axis and a view index axis so that the view-to-view variation of the positions of channels in the detector rows relative to the axis of translation due to the tilt of the scan plane is canceled out;
  a data extracting device for extracting a range of data in which data are completely present for all the views in the view direction from the shifted data array;
  a dummy data appending device for appending the extracted data with dummy data to adjust the data range; and
  a data transformation device for transforming the data into data enabling alignment of the channel positions through all views.

11. The X-ray CT apparatus of claim 10, wherein
said data position shifting device shifts the positions of parallelized data of the channels in a j-th (j is the detector row index and $1 \leq j \leq J$) detector row by $$j\_delt\_iso = Lj^* \tan \theta^* \sin\{2\pi(pvn-1)/VWN\}$$

in the channel direction, where pvn is the view index and $1 \leq pvn \leq VWN$, rotation is made substantially for $2\pi$ for all views, the tilt angle is represented as $\theta$, and a distance from an intersection of the axis of translation and the axis of rotation to a scan plane corresponding to the j-th detector row is represented as Lj.

12. The X-ray CT apparatus of claim 11, wherein
said data extracting device extracts data from a (Roundup$\{Lj^* \tan \theta/DMM\}+1+j\_delt\_iso$)-th channel to a (I—Roundup$\{Lj^* \tan \theta/DMM\}-1+j\_delt\_iso$)-th channel in the j-th detector row for a pvn-th view, where DMM is the channel-to-channel distance, and Roundup $\{\ \}$ is a roundup function.

13. The X-ray CT apparatus of claim 10, wherein said data transforming device is interpolating device.

14. The X-ray CT apparatus of claim 10, wherein said dummy data are air data.

15. An X-ray CT apparatus comprising:
an X-ray tube;
a multi-row detector having more than one detector row opposed to said X-ray tube;
a translation control device for translating said X-ray tube and said multi-row detector along an axis of translation relative to a subject;
a rotation control device for rotating at least one of said X-ray tube and said multi-row detector around an axis of rotation;
a tilt control device for tilting the angle of a scan plane formed by said rotation relative to the axis of translation to an angle other than 90°;
a scan control device for collecting data by a helical scan employing said
multi-row detector with the scan plane tilted;
an image producing device for producing an image based on the collected data;
a preprocessing device for applying preprocessing to said data;
a tilt correcting processing device for applying tilt correcting processing for correcting view-to-view variation of the positions of channels in the detector rows relative to the axis of translation due to the tilt of the scan plane, wherein said tilt correcting device comprises:
  a data position shifting device for shifting the positions of data arranged in a two-dimensional array along a channel index axis and a view index axis so that the view-to-view variation of the positions of channels in the detector rows relative to the axis of translation due to the tilt of the scan plane is canceled out;
  a data extracting device for extracting a range of data in which data are completely present for all the views in the view direction from the shifted data array;
  a dummy data appending device for appending the extracted data with dummy data to adjust the data range; and
  a data transformation device for transforming the data into data enabling alignment of the channel positions through all views;
a multi-slice/helical interpolation processing device for applying multi-slice/helical interpolation processing for calculating interpolated data from proximate data in an image reconstruction plane; and
a backprojection processing device for applying backprojection processing to the interpolated data to produce an image.

16. An X-ray CT apparatus comprising:
an X-ray tube;
a multi-row detector having more than one detector row opposed to said X-ray tube;
a translation control device for translating said X-ray tube and said multi-row detector along an axis of translation relative to a subject;
a rotation control device for rotating at least one of said X-ray tube and said multi-row detector around an axis of rotation;
a tilt control device for tilting the angle of a scan plane formed by said rotation relative to the axis of translation to an angle other than 90°;
a scan control device for collecting data by a helical scan employing said
multi-row detector with the scan plane tilted;
an image producing device for producing an image based on the collected data;
a preprocessing device for applying preprocessing to said data;
a tilt correcting processing device for applying tilt correcting processing for correcting view-to-view variation of the positions of channels in the detector rows relative to the axis of translation due to the tilt of the scan plane, wherein said tilt correcting device comprises:
  a data extracting device for extracting data from a (Roundup$\{Lj^* \tan \theta/DMM\}+1+j\_delt\_iso$)-th channel to a (I—Roundup$\{Lj^* \tan \theta/DMM\}-1+j\_delt\_iso$)-th channel in a j-th (j is the detector row index and $1 \leq j \leq J$) detector row for a pvn-th view, where pvn is the view index and $1 \leq pvn \leq VWN$, rotation is made substantially for $2\pi$ for all views, the tilt angle is represented as $\theta$, a distance from an intersection of the axis of translation and the axis of rotation to a scan plane corresponding to the j-th detector row is represented as Lj, DMM is the channel-to-channel distance, Roundup { } is a roundup function, and $j\_delt\_iso = Lj * \tan\theta * \sin\{2\pi(pvn-1)/VWN\}$ a dummy data appending device for appending the extracted data with dummy data to adjust the data range; and a data transformation device for transforming the data into data enabling alignment of the channel positions through all views;

a multi-slice/helical interpolation processing device for applying multi-slice/helical interpolation processing for calculating interpolated data from proximate data in an image reconstruction plane; and a backprojection processing device for applying backprojection processing to the interpolated data to produce an image.

\* \* \* \* \*